United States Patent [19]

Ritter et al.

[11] Patent Number: 5,338,494
[45] Date of Patent: Aug. 16, 1994

[54] METHOD OF INSPECTION WITH COLD LIGHT PENETRANT

[75] Inventors: Michael P. Ritter, Glendora; William H. Long, Lytle Creek, both of Calif.

[73] Assignee: Rockwell International Corporation, Seal Beach, Calif.

[21] Appl. No.: 922,441

[22] Filed: Jul. 31, 1992

[51] Int. Cl.$^5$ .................... C09K 3/00; G01N 31/00
[52] U.S. Cl. ........................................ 252/700; 436/5
[58] Field of Search ............ 436/5; 252/700; 427/8, 427/157

[56] References Cited

U.S. PATENT DOCUMENTS

| | | | |
|---|---|---|---|
| 2,259,400 | 10/1941 | Switzer | 436/5 |
| 3,744,295 | 7/1973 | Allinikou | 252/586 |
| 4,054,535 | 10/1977 | Molina | 252/301.19 |
| 4,365,516 | 12/1982 | Molina | 436/5 |
| 4,462,931 | 7/1984 | Cohen et al. | 252/700 |
| 4,642,294 | 2/1987 | Arnaud et al. | 436/5 |
| 4,774,188 | 9/1988 | Chandross | 436/5 |
| 5,242,830 | 9/1993 | Argy et al. | 436/5 |

*Primary Examiner*—Philip Tucker
*Attorney, Agent, or Firm*—Terrell P. Lewis; Charles T. Silberberg

[57] ABSTRACT

A method and composition facilitating the inspection of structural surfaces, such as fuel tank walls, to identify or locate cracks, flaws and other defects. The composition is a system of materials including a dye-containing penetrant material and a chemiluminescent material which reacts with the dye in the penetrant material. The method involves application of the two materials sequentially such that they react chemically to produce light which is visible to the naked, unaided eye, thereby eliminating the need for electrically-powered or "hot" light.

3 Claims, No Drawings

METHOD OF INSPECTION WITH COLD LIGHT PENETRANT

The invention described herein was made in the performance of work under USAF Contract No. F33657-81-C-0208, and the U.S. Government has certain rights in this invention.

BACKGROUND OF THE INVENTION

1. Field of the Invention

The present invention relates to processes and compositions for non-destructively testing surfaces of materials to locate defects, and is specifically adapted to processes for determining the surface integrity of fuel tanks without the introduction or use of an electrically powered or "hot" light source.

2. Background of the Invention

One of the areas of increasing concern in the aerospace industry today is the integrity of fuel tank structures. Often, during or after flight, surface defects, such as cracks and holes, are discovered. Inspection of the tank surfaces, both inside and out, must be undertaken in order to locate these defects.

Penetrants incorporating a dye component have long been known and used to detect surface defects, such as cracks in workpiece surfaces. Examples of such penetrant compositions are disclosed in U.S. Pat. Nos. 4,392,982, 4,186,304 and 3,915,886.

Typically, dye penetrant is applied to the surface to be inspected in liquid or solid form, after which the surface is superficially cleaned to remove excess dye and to leave only residual dye on minute quantities which are retained within the surface voids or defects. Depending on the composition of the penetrant, an emulsifying agent or solvent is sometimes used to transform excess penetrant as necessary for solubility of the penetrant in the cleaning solution. Cleaning is often done by scrubbing the surface with a sponge or cloth saturated with the emulsifying agent or cleaning solution, or both.

In the past, the dye used in the inspections consists of a fluorescent material which Is applied to the surface to be inspected. The inspections then must be carried out using a "hot" light, as for example an electrically powered ultraviolet or fluorescent light source. Once application of the penetrant has been appropriately carried out, it is possible to determine the location and nature of surface defects or flaws by directing the "hot" light onto the treated surface and noting the areas of the surface where the penetrant material is visible.

Quite understandably, there is much concern for human safety when an inspection of fuel tanks is performed with hot light, since almost all aerospace fuel vapors are extremely volatile and explosive. Moreover, innumerable safety precautions must be taken or standards complied with in order to protect against explosion of the fuel and consequent damage to property or loss of life. For these reasons, as well as the desire to eliminate the inordinately high cost associated with the equipment and procedures used in carrying out these inspections, it has become most desirable to find alternative flaw detection/inspection methods and/or apparatus for use in environments where volatile substances have been contained, so that the danger of fire or explosion is substantially eliminated.

OBJECTS OF THE INVENTION

It is therefore an object of the present invention to provide an improved method for inspecting surfaces of fuel tanks to locate flaws or defects which will overcome all the drawbacks and disadvantages of the previously-known penetrant inspection methods.

Another object of the present invention is to provide a method for detecting flaws in fuel tank surfaces using a "cold" light and a penetrant capable of emitting light visible to the naked, unaided eye.

These and other objects are accomplished by the application of a system of materials to the surfaces of fuel tanks, the system including a dye-containing penetrant and a luminescing composition which chemically reacts with the penetrant to yield the visible light.

DETAILED DESCRIPTION OF THE INVENTION

It has long been recognized that "cold" light is vastly different from "hot" light. "Cold" light is the result of a chemical or bio-chemical process. Biochemical light is best exemplified by the light of a firefly. Chemical light, or chemiluminescence, involves the conversion of the energy released in a chemical reaction directly to light without the involvement of heat or flame. "Hot" light is best illustrated by the light emanating from a campfire or an incandescent bulb.

The most efficient case of cold light production Is where each molecule of a chemiluminescent reactant produces one photon of light. The firefly approaches this theoretical limit by producing 88 photons for each 100 molecules for a quantum yield of 88%. Research in this technology has produced reactions rivaling the firefly.

Incandescence involves the conversion of chemical energy to heat, followed by conversion of some of the heat energy to light. Chemical light or chemiluminescence differs in that chemical energy Is converted directly to light without the involvement of heat as an intermediate energy form. Conversion of chemical energy to heat in chemical reactions is commonly observed and well understood. Light is just as legitimate a form of energy as heat, but conversion of chemical energy to light is a rare phenomenon.

Chemiluminescence requires a combination of two special kinds of chemistry. The first, called fluorescence, occurs when a molecule absorbs light to become an electronic excited state. After a very short time, e.g. one billionth of a second, the excited state releases its energy as light. Chemiluminescence includes this fluorescent process except that the necessary excited state is a product of chemical reaction. The second kind of chemistry is the chemical reaction that produces the excited state. This is called the excitation process and is the real key to chemiluminescence.

An excitation reaction must be capable of generating at least 40 to 70 kilocalories per mole of energy, the energy range of visible light. This a substantial amount of energy in chemical terms, and only highly energetic molecules are capable of meeting this requirement. Not only must the energy be available, but it must be provided essentially instantaneously in a single chemical step.

In addition to substantial instantaneous energy release and the formation of a fluorescent product, other requirements must be met which involve the distribution of energy released from a reaction between light emitting (or electronic) excited states and heat emitting (or vibrational) excited states. Since all of these requirements must be met together in an efficient chemiluminescent reaction, and since none of the requirements are commonly met even individually, it is understandable that efficient chemiluminescence is rare.

it is known in the prior art to combine materials in a specific manner to produce a chemiluminescent composition. Use of these materials is contemplated by the method of the present invention.

The prior art process involves a first step using essentially conventional chemistry to produce a key intermediate material, a second step involving the critical excitation process where the chemical energy of the intermediate material is converted and transferred to electronic excitation energy in a separate fluorescent chemical molecule (a "fluorescer"), and a third step involving conventional fluorescent emission.

The critical aspect of the process is the structure of the intermediate material. Its efficiency is believed to result, in part, from its high energy content, its ability to release its energy instantaneously through a concerted peroxide decomposition reaction, the quantum mechanical reluctance of a small molecule like carbon dioxide to accept a large amount of the chemical energy as heat, and the inability of carbon dioxide itself to become electronically excited by the available energy. The intermediate material exhibits an appreciable lifetime, yet because of its energy content, it decomposes when it encounters a fluorescer with the ability to accept its energy. The fluorescer thus acts as a catalyst for the decomposition of the intermediate material. Because the fluorescer is separate from the energy producing components of the reaction, it is able to be varied without changing the basic chemistry.

The process thus described is characterized as a peroxyoxalate chemiluminescent system. Since the color of the light emitted depends solely on the fluorescer material selected, it is understood that the peroxyoxalate chemiluminescent could be formulated to provide any color desired.

The present invention is a method which facilitates the inspection of surfaces of structures, such as fuel tank walls, to identify or locate cracks, flaws and other defects. The invention embraces a system of materials including a dye-containing penetrant material, such as is disclosed in U.S. Pat. Nos. 3,748,469, 3,777,157, 3,838,160, 3,915,886, 3,989,949, 4,186,304 and 4,392,982 (all issued to Molina), and a chemiluminescent material of the type described above. In addition, the invention is a method for applying the system of materials to the surfaces of a structural member to identify and/or locate cracks or defects in the surfaces which would diminish the integrity of the member for its intended purpose.

In accordance with the present invention, the process facilitates the identification of flaws or defects in a surface through the application to the surface of the aforementioned dye-containing penetrant and chemiluminescent materials. These materials, applied to the surface in essentially two steps, chemically react to generate light which is visible to the unaided eye.

The first step of tile process involves the application of the penetrant composition (part "A") to the area to be inspected. The manner of application is one which is well-known in this art. Following application of this first (part "A") material, the treated surface is wiped with a dry cloth, and then wiped with a cloth dampened with a slightly basic solution to minimize the luminescing capability of the material left on the surface. Optimally, all material on the surface, as opposed to in the cracks, would be removed at this point.

The second step of the process involves the application of the chemiluminescent-containing composition (part "B") to the surface being inspected.

In those areas of the surface where flaws have trapped residual amounts of the first composition, the second composition contacts and provides a reaction with the first composition. This reaction is the result of a chemical interaction of the two compositions with an attendant outcome of the reaction being a release of visible light. Appropriate choice of the compositions leads to variation of the color of light emitted, a desired degree of brightness, duration of activity and system sensitivity.

The process performed according to the teachings of the present invention negates the need for any external source of illumination, as for example the source of "black" or "hot" light typically required for illumination of conventional fluorescent penetrants.

The chemiluminescent materials contemplated are nontoxic and present no more corrosive danger than the penetrant being used. Sensitivity control is achieved by altering the viscosity of the chemiluminescent material, as for example by adding carboxymethal cellulose as a thickening agent.

While certain representative embodiments and details have been shown for the purpose of illustrating the invention, it will be apparent to those skilled in this art that various changes and modifications may be made therein without departing from the spirit or scope of this invention.

What we claim is:

1. A method for performing penetrant inspection of a surface without the use of an external light source to identify and determine the nature of flaws or defects in the surface, comprising:

applying a first penetrant composition to the surface being inspected, applying a second luminescing composition atop said first composition which chemically reacts with the first composition to cause emission of visible light, whereby surface flaws or defects trap a sufficient amount of the first composition to permit reaction to occur with the second composition when the latter is applied over the first composition, thereby resulting a chemical reaction which yields visible light so that said flaws or defects can be identified and located.

2. The method of claim 1, wherein said first penetrant composition contains a dye material.

3. The method of claim 1, and further including the step of applying a base solution atop said first composition.

* * * * *